United States Patent [19]

Nasiff

[11] Patent Number: 4,757,453
[45] Date of Patent: Jul. 12, 1988

[54] BODY ACTIVITY MONITOR USING PIEZOELECTRIC TRANSDUCERS ON ARMS AND LEGS

[76] Inventor: Roger E. Nasiff, 9422 LeBeau La., Brewerton, N.Y. 13029

[21] Appl. No.: 843,589

[22] Filed: Mar. 25, 1986

[51] Int. Cl.$^4$ .................. A61B 5/10; G06F 15/42
[52] U.S. Cl. .................. 364/415; 128/782; 272/DIG. 5
[58] Field of Search ............ 272/93, DIG 5, DIG. 6, 272/DIG. 9; 364/413, 415; 128/782

[56] References Cited

U.S. PATENT DOCUMENTS

| 4,192,000 | 3/1980 | Lipsey | 364/415 |
| 4,353,375 | 10/1982 | Colburn et al. | 128/782 |
| 4,409,992 | 10/1983 | Sidorenko et al. | 128/782 |
| 4,525,074 | 6/1985 | Murakami | 368/10 |

FOREIGN PATENT DOCUMENTS 0578061 10/1977 U.S.S.R. .................. 128/782

OTHER PUBLICATIONS

Dewhurst, D. J., "Characterisation of Human Limb Movements by Accelerometry", *Med. & Biol. Eng. & Comput.*, vol. 15, Jul. 1977, 462–466.

*Primary Examiner*—Jerry Smith
*Assistant Examiner*—Clark A. Jablon

[57] ABSTRACT

Clamping a piezoelectric transducer onto the arm produces a signal whose integration with respect to time corresponds directly to the energy produced by the arm's movement. By clamping four (4) such transducers onto the body, one on each arm and one on each leg, the total integration of the four (4) signals gives a measure of the total energy spent in motion by the body. The desired body energy spent can be displayed quantitatively by first converting the integrated signal into a pulse train, then counting the pulses, and then driving a display with the counter's value.

2 Claims, 8 Drawing Sheets

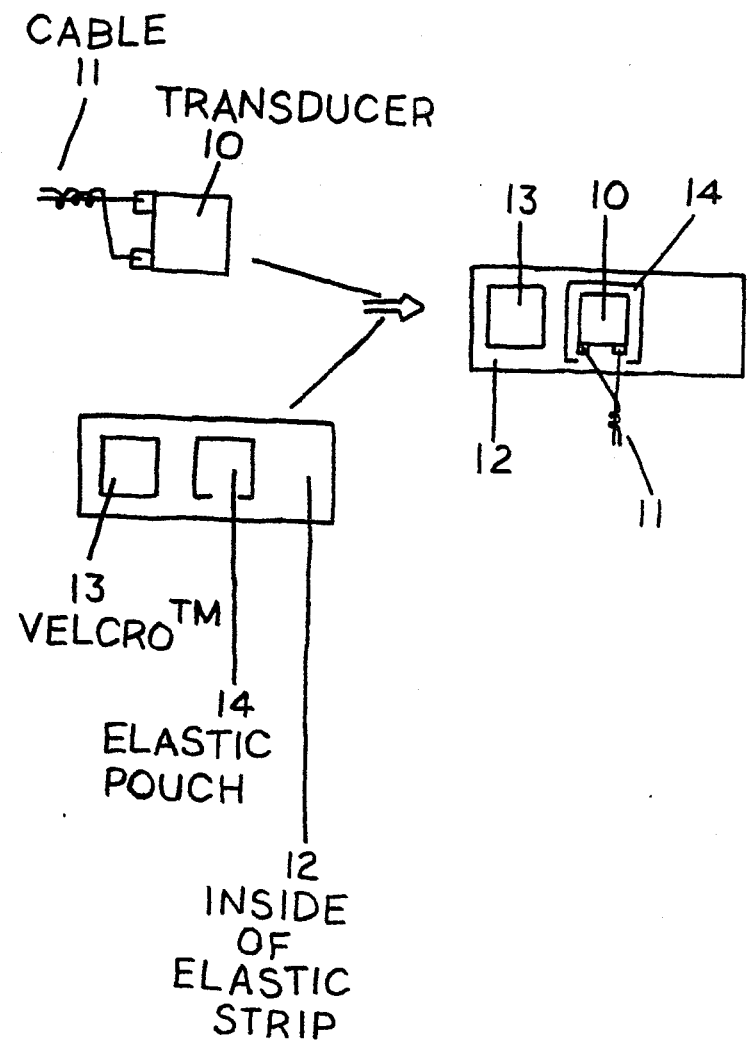

SHEET 3 OF 8
ROGER NASIFF
FIGURE 1(c)
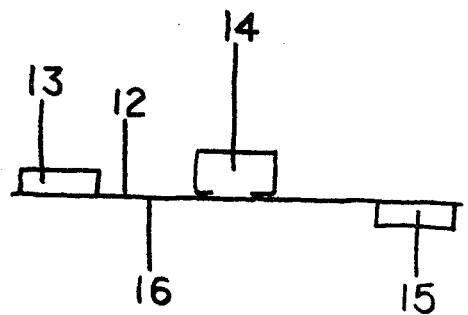
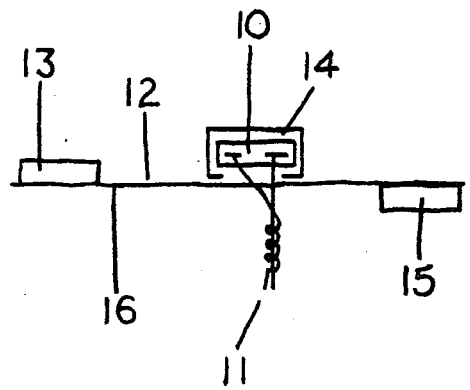

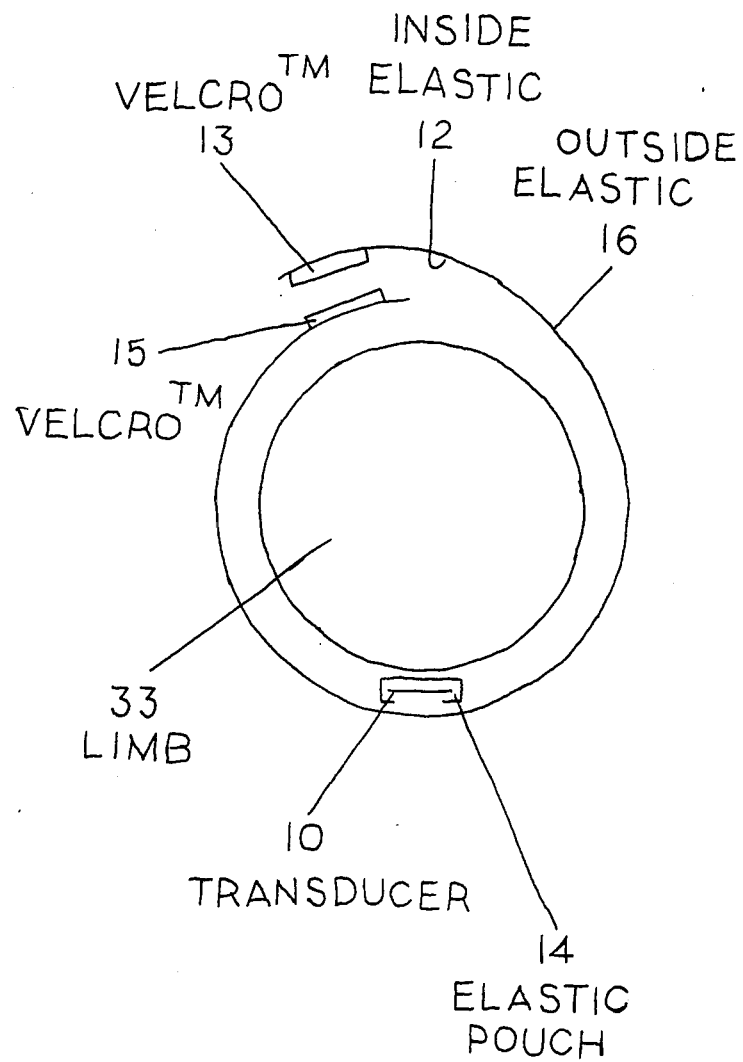

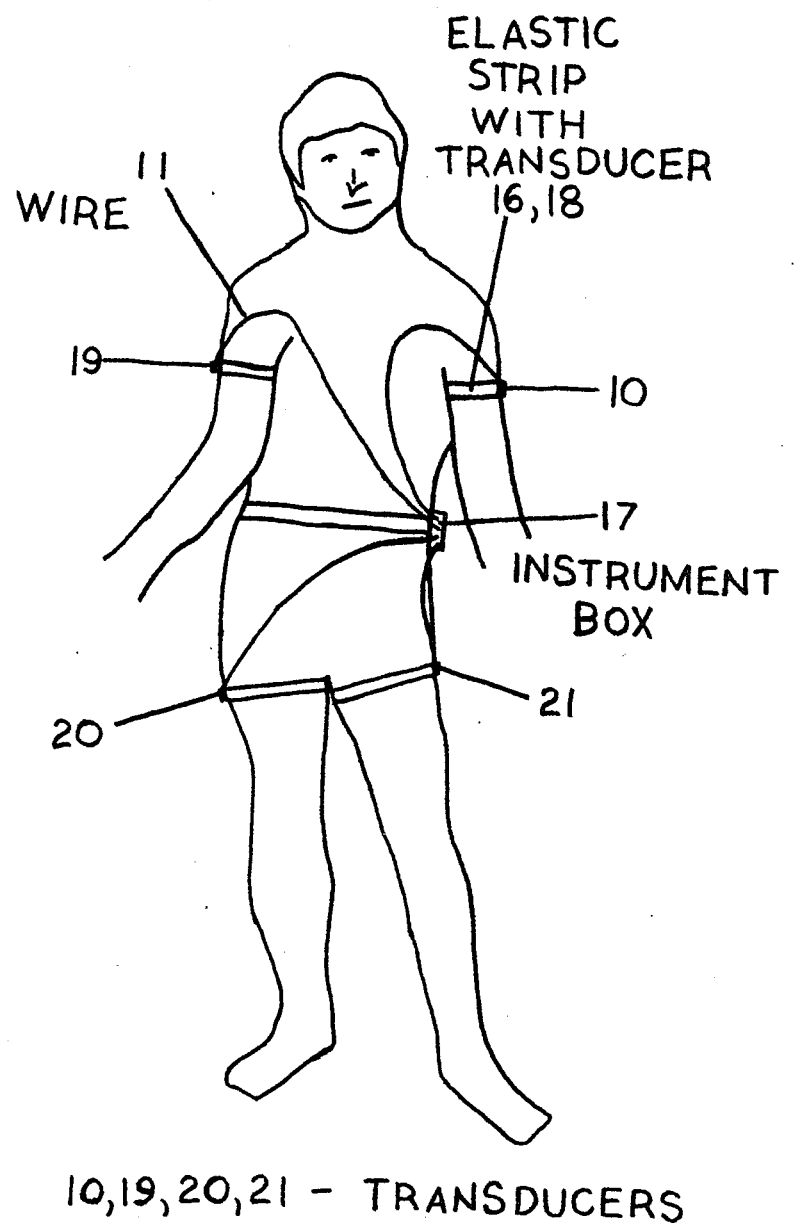

$$AREA = \int V_o(T) DT$$

BODY ACTIVITY MONITOR USING PIEZOELECTRIC TRANSDUCERS ON ARMS AND LEGS

BACKGROUND OF THE INVENTION

A. Field of Invention

This invention pertains to the field of biomedical data processing. More specifically, this invention pertains to the field of body activity measurement using multiple activity/pressure detecting transducers, such as piezoelectrics.

B. Description of Prior Art

1. Problem Statement/Objects of Invention

Ideally, for a body activity monitor to be technically and economically suitable for extended periods of time and during all normal daily activities, it should be accurate, repeatable, easy to manufacture, simple in structure, inexpensive, easy to use, give continuous activity expenditure data, be comfortable to the patient, be low in power consumption, be small in size, have very few environmental restrictions on its usage, be easily applied to the patient, be easy to calibrate, be reliable, and measure activity as directly as possible (to maximize activity data correlation and minimize secondary effect correlations that cause errors with indirect methods).

2. Prior Art Performance

Most of the small in size, portable prior art appear to satisfy most of the requirements of the instant invention, except accuracy and repeatability. Much of this is due to the simple switch or accelerometer transducers being placed at the waist.

At first glance, putting the transducer in a box at the waist has three major advantages:

a. Major energy consuming activities have motions at the at the waist, so a waist-located sensor should indicate the general trend of the body's energy expenditure during motion.

b. The box should protect the sensor from being broken or from being taken out of calibration.

c. If only one sensor is used, only one sensor needs to be built and only one sensor channel needs to be calibrated.

The researchers who developed these devices have shown that these methods commonly underestimate energy expenditures for some major activities by as much as a factor of 3 and overestimate other activities by as much as a factor of 2.

These problems are fundamentally due to these methods not measuring the activity of the major activity generating parts of the body: the arms and legs. For example, if these devices are calibrated at a mid-speed walking activity, they overestimate jumping rope and running and underestimate toe touching, sit-ups, and leg lifts.

Documentation to support the above prior art description can be found in the following publications:

a. U.S. Pat. No. 4,192,000. (filed 1977, issued 1980). Cl. 364-415. Elmer M. Lipsey. Electronic Calorie Counter. This device uses a magnetic sensor at the waist to measure motion.

b. Other Sources.

Hemokinetic Inc. (2923 Osmundsen Rd., Madison, WI. 53711). This company produces a device called Caltrac which is the marketed version of Servais, Webster, and Montoye's device.

Servais, Webster, and Montoye. "Estimating Human Energy Expenditure Using an Accelerometer Device." J. of Clinical Engineering. April-June 1984. Uses a piezoelectric bender as an acceleration detecting sensor at the waist. Assumes (incorrectly) that body energy expenditure is linearly proportional to acceleration at the waist.

Wong, Webster, Montoye, and Washburn. "Portable Accelerometer Device for Measuring Human Energy Expenditure." IEEE Trans. Biomedical Engineering. June 1981. Precursor to the 1984 Servais, Webster, and Montoye device. Uses a waist worn modified ceramic phonocartridge as the transducing element.

3. This Invention's Performance

This invention is different and better than the prior art because it solves all of the problems listed earlier; especially accuracy and repeatability. It measures the work done by the major moving elements of the body. (energy=the change in work=force times distance). Pressure/force piezoelectric transducers measure the force and speed that the elements are experiencing and also the time that the elements are moving. (since energy=the force times distance=force times speed times time, we are measuring energy directly).

SUMMARY OF THE INVENTION

A. Reason for the Invention

The market needs a technically and economically suitable body activity monitor to be used for extended periods of time and during all normal daily activities. Among the requirements of the suitable instrument are its abilities to be accurate, be repeatable, be easy to manufacture, be simple in structure, be inexpensive, be easy to use, give continuous energy expenditure data, be comfortable to the patient, be easy to calibrate, be reliable, be low in power consumption, be small in size, have very few environmental restrictions on its usage, be easily applied to the patient, and measure body activity as directly as possible.

B. Invention Function

This invention fulfills the above requirements by functioning in a simple manner and by being composed of inexpensive and easily manufactured components.

1. Transduction of the Body Activity Waves to Electrical Voltage Waves.

If we clamp a pressure transducer to the arm and then move the arm, the pressure transducer's inertia will cause it to resist the motion. Consequently, a force will exist between the arm and transducer. If we design the transducer response time constant to be longer than the arm motion times, the force/pressure measured will exist long enough throughout the arm motion to indicate quantitatively the energy spent during the arm motion.

If the transducer is a piezoelectric material, an electrical signal is produced directly by the piezoelectric converting the mechanical waves into electrical voltage and charge waves. Either the voltage or charge waves can be measured from the piezoelectric using well known high input impedance voltage or charge-to-voltage amplifiers, respectively.

In order to measure the total body activity (=energy spent in motion), the instant invention uses four (4) piezoelectric transducers: one for each arm and one for each leg. This arrangement allows us to detect and quantify almost all major body activities (more transducers could be used, but the discomfort to the patient may outweigh the added accuracy).

2. Application of the Electrical Voltage Waves to Yield Body Activity Data.

Integrating the waveforms from the four (4) sensors together yields a waveform that represents the total body energy output as motion. This integrated waveform can drive a voltage-to-pulse train circuit to practically add the 'energy unit' output (e.g. calories, joules, ergs). A constant running counter can add these pulses over a long period of time to give the operator the total activity energy output by the body over the long period. The calibration of this system (e.g. the number of pulses to send to the counter per volt-sec of waveform) depends on the specific voltages used and the units of energy (e.g. calories) desired.

BRIEF DESCRIPTION OF THE DRAWINGS

The following figures have been included to clearly describe the invention from mechanical arrangement views, electrical circuit views, graphical data relationship views, and practical system implementation views.

FIGS. 1(a)–1(d) are a series of views of the transducer and its placement in the elastic strips.

FIG. 2 is a drawing showing the placement of the transducers on the patient.

DESCRIPTION OF THE PREFERRED EMBODIMENT

Figure 1B:
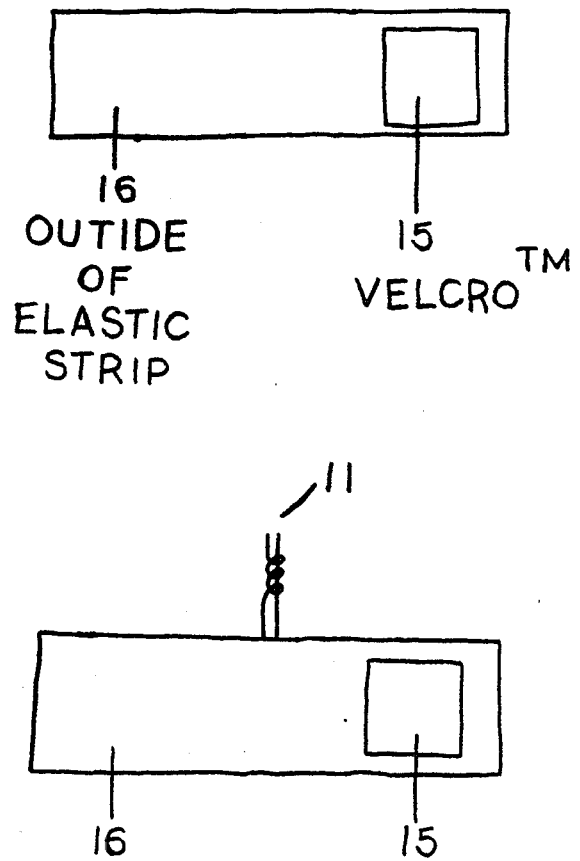

The piezoelectric transducer and its placement in the elastic strips are shown in FIG. 1. Item 10 is the piezoelectric pressure transducer. Item 11 is the two (2) conductor cable from the transducer. Item 12 is the inside (the side that makes contact with the patient) of the elastic strip that holds the transducer against the patient. Item 13 is one type of Velcro TM: item 15 is the other type of Velcro TM that sticks to item 13. Item 14 is an elastic pouch, attached to the elastic strip, that holds the transducer to the elastic strip. Item 16 is the part of the elastic strip that is seen when looking at the patient with an elastic strip attached. Item 33 is a cross-sectional view of an arm with a transducer and its elastic strip wrapped around it to show how the transducer assembly is applied.

FIG. 2 is a frontal view of a patient with all four (4) transducers in place. Item 18 is the left arm transducer assembly. Item 19 is the right arm transducer assembly. Item 20 is the right leg transducer assembly. Item 21 is the left leg transducer assembly. Item 17 is the instrument box where the transducer cables plug into the analog circuitry.

Figure 3:
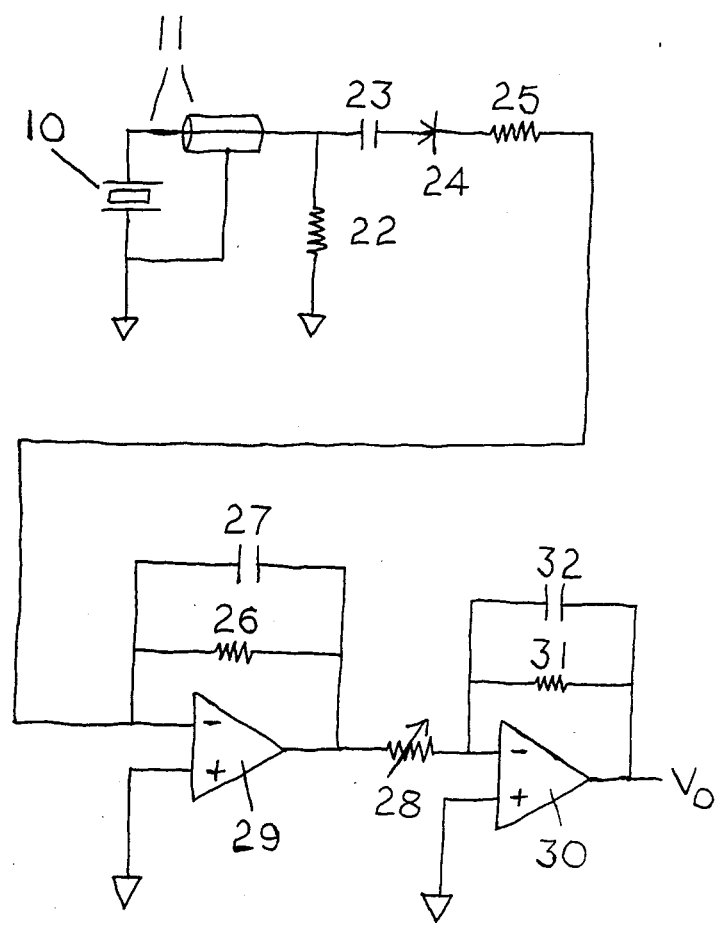
FIG. 3 is a schematic representation of the first analog signal processing stage for each channel.

FIG. 3 is a schematic of an analog transducer interface circuit. It converts the small bipolar, possibly noisy transducer signal into a relatively large unipolar, minimal noise output voltage at Vo. Item 22 provides an optional current leakage path from the transducer if drift is a problem. Items 23 (a capacitor), 24 (a diode), and 25 (a resistor) produce a rectified high pass filter to yield a unipolar, low baseline drift signal. Items 26 (a resistor), 27 (a capacitor), and 29 (an op amp) produce a low pass filter amplifier to lower noise and amplify the signal. Items 28 (a variable resistor/potentiometer), 31 (a resistor), 32 (a capacitor), and 30 (an op amp) produce a variable gain low pass filter amplifier to lower noise and calibrate the output signal Vo to the units of energy wanted.

Figure 4:
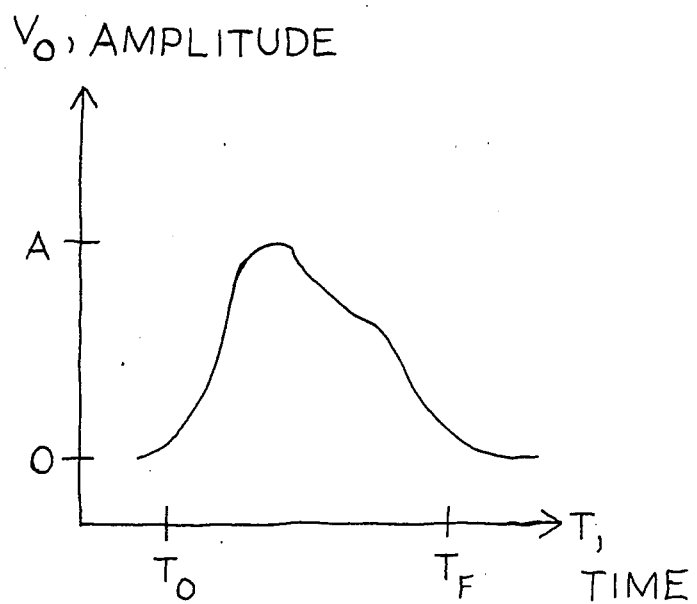
FIG. 4 is a graphical drawing of the general characteristics of the signal output from the analog circuit stage.

FIG. 4 is a graphical representation of a typical signal output from the analog circuit in response to a single limb motion (e.g. the lifting of the left arm). The area under the Vo(t) curve from To to Tf is directly proportional to the energy spent in activity as described earlier.

Figure 5:
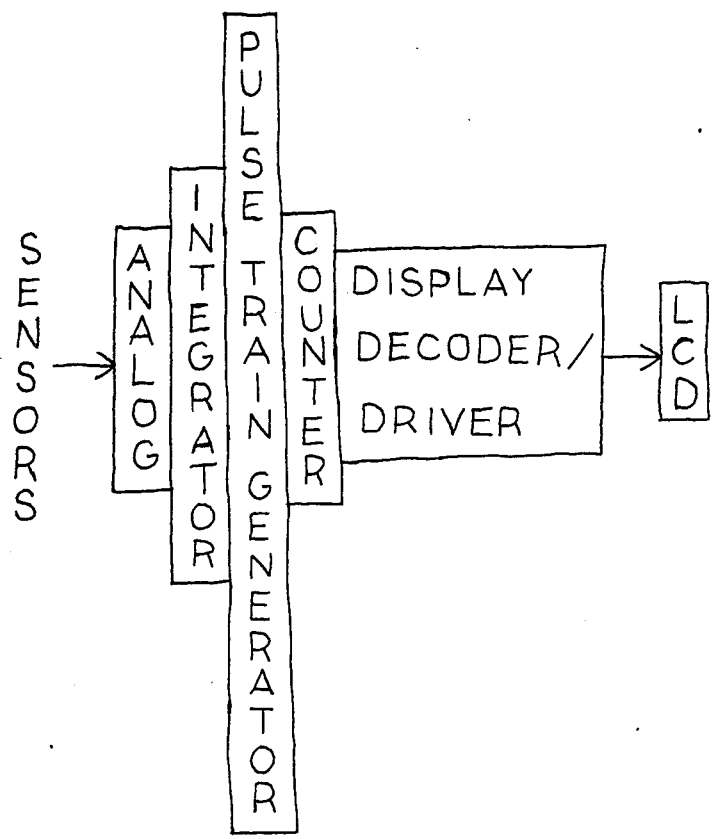
FIG. 5 is a block diagram of a practical system implementation of the invention.

FIG. 5 is a block diagram of a practical system implementation of the invention. Upon power up, the pulse counter is reset, clearing the LCD. As the arms and legs move, the LA (left arm), RA (right arm), LL (left leg), and RL (right leg) sensors send signals to their analog circuits. The analog signals are integrated together and the resultant signal is converted to a series of pulses directly proportional to the amount of activity energy detected. The pulses are counted, and the amount of energy detected is displayed numerically on the LCD.

The foregoing description taken together with the appended claims constitute a disclosure such as to enable a person skilled in the biomedical data processing art and having the benefit of the teachings contained therein to make and use the invention. Further, the structure herein described meets the objects of invention and generally constitute a meritorious advance in the art unobvious to such a person not having the benefit of these teachings.

Obviously, many modifications and variations of the present invention are possible in the light of the above teachings, and, it is therefore understood that within the scope of the disclosed inventive concept, the invention may be practiced otherwise than as specifically described.

What is claimed is:

1. The method of directly transducing the body activity waves from the body limbs, comprising the steps of:
   connecting a piezoelectric transducer to an elastic strip to form a transducer assembly,
   applying one said transducer assembly on each of the four (4) major body limbs, and
   converting each of the transducer signals into unipolar voltage waveforms directly proportional to the activity energy they represent.

2. The method of claim 1 wherein the body activity energy is quantified and displayed, comprising the steps of:
   integrating the four (4) said unipolar voltage waveforms to produce a pulse train that represents the total energy from all four said transducers,
   adding the said pulses by means of a counter, and
   driving a display with the said counter's value to, as an end result, display the energy output by the body's activity, in calibrated units.

* * * * *